United States Patent [19]

Suzuki et al.

[11] Patent Number: 4,657,912

[45] Date of Patent: Apr. 14, 1987

[54] GRANULAR BAIT COMPOSITIONS FOR THE CONTROL OF ANTS EMPLOYING A PYRIMIDINONE DERIVATIVE IN COMBINATION WITH GROUND PUPA OF SILKWORM

[75] Inventors: Munehiro Suzuki, Toyohashi; Masaomi Kimpara, Hamamatsu; Kiyoshi Tsuda, Kagoshima, all of Japan

[73] Assignee: American Cyanamid Company, Stamford, Conn.

[21] Appl. No.: 839,774

[22] Filed: Mar. 18, 1986

Related U.S. Application Data

[63] Continuation-in-part of Ser. No. 723,401, Apr. 15, 1985, abandoned.

[51] Int. Cl.$^4$ .................... A01N 25/00; A01N 43/54
[52] U.S. Cl. ...................... 514/275; 424/84
[58] Field of Search ............. 514/275; 424/84

[56] References Cited

U.S. PATENT DOCUMENTS

| | | | |
|---|---|---|---|
| 4,213,988 | 7/1980 | Lovell | 514/375 |
| 4,320,130 | 3/1982 | Balsley et al. | 424/84 |
| 4,323,556 | 4/1982 | Dal Moro et al. | 424/84 |
| 4,353,907 | 10/1982 | Lovell | 514/275 |

FOREIGN PATENT DOCUMENTS

| | | | |
|---|---|---|---|
| 2067408 | 7/1981 | United Kingdom | 514/275 |
| 2070430 | 9/1981 | United Kingdom | 514/275 |
| 2081096 | 2/1982 | United Kingdom | |

*Primary Examiner*—Allen J. Robinson
*Attorney, Agent, or Firm*—Susan H. Rauch

[57] ABSTRACT

The invention is pesticidal granular bait compositions useful for the control of ants and a method of controlling ants using the composition.

12 Claims, No Drawings

GRANULAR BAIT COMPOSITIONS FOR THE CONTROL OF ANTS EMPLOYING A PYRIMIDINONE DERIVATIVE IN COMBINATION WITH GROUND PUPA OF SILKWORM

This application is a continuation-in-part of copending U.S. Ser. No. 723,401 filed. Apr. 15, 1985 now abandoned.

The present invention relates to insecticidal granular bait compositions useful for the control of ants, containing tetrahydro-5,5-dimethyl-2-(1H)-pyrimidinone-{3-[4-(trifluoro-methyl)phenyl]-1-{-2-[4-(trifluoromethyl)-phenyl]ethenyl}-2-propenylidene}hydrazone or fatty acid salts thereof as the toxicant and ground pupa of silkworm as the attractant. The insecticide which is active as a stomach poison, hereinabove named, can be graphically illustrated by formula (I)

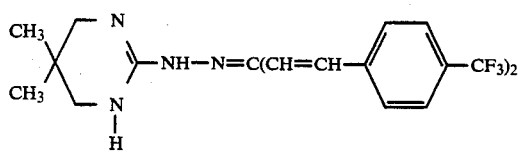

and the fatty acid salts thereof.

The insecticide is disclosed in U.S. Pat. No. 4,163,102 and its method of use is disclosed in U.S. Pat. No. 4,213,988, all of which are incorporated herein by reference. Insecticidal bait compositions of the above-named insecticide are disclosed in U.S. Pat. No. 4,320,130, which describes solid corn based baits which are suitable for application over large areas for the control of insects.

The composition may contain from 0.5% to 5% of the formula (I) insecticide and 95% to 99.5% dry pupa of silkworms.

A preferred embodiment of the invention is compositions comprising on a weight basis 15% to 70% dry pupa of silkworms, 0.5% to 5% of the formula (I) insecticide, 0.0% to 5.0% of a fatty acid such as oleic acid and 29.5% to 75.0% of a solid and/or liquid carrier or mixture of carriers and an antimicrobial and/or an antioxidizing agent. Examples of carriers are fishmeal, powdered sugar, flour, rice bran oil, corn oil, soybean oil, corn syrup, glucose, krill and the like. These compositions are exceedingly effective for attracting a variety of ants to the bait compositions and subsequently controlling the ants.

A more preferred embodiment of the invention is compositions comprising on a weight basis 30% to 50% of dry pupa of silkworms, 0.5% to 3.0% of formula (I) insecticide, 10% to 20% fishmeal, 25% to 40% powdered sugar, 0.1% sodium salicylate, 0.2% tert-butylhydroquinone, and 0.1% of the sodium salt of carboxymethylcellulose.

Pupa of silkworms, is a byproduct of the silk industry obtained during the isolation of silk.

Compositions of the invention may readily be prepared by grinding the dry pupa by conventional methods to maximize the yield of 10 to 60 mesh particles, which is preferred.

A solution of the formula (I) insecticide or a fatty acid salt thereof such as the oleic acid salt, in an appropriate solvent such as corn oil, rice oil, or soybean oil may then be sprayed onto the tumbling dry pupa particles. Additional edible carriers such as fishmeal, sugars, and flour, may then be added and the mixture blended until homogeneous. Optionally antimicrobial agents such as sodium salicylate, sodium dehydroacetate and sodium benzoate may be added to inhibit microorganism growth or antioxidants such as tertbutylhydroquinone, n-propyl gallate, 3-tert-butyl-4-hydroxy anisole, and butylated hydroxytoluene may be incorporated during the blending of the compositions to improve the storage characteristics of the final compositions, as can other agents such as thickening agents and the like.

The invention includes a method for controlling ants comprising applying in the vicinity of their habitat or infested area a granular insecticidal bait composition comprising tetrahydro-5,5-dimethyl-2-(1H)-pyrimidinone-{-3-[4-trifluoromethyl)phenyl]-1-{-2-[4-trifluoromethyl)phenyl]ethenyl}-2-propenylidene}hydrazone having the formula (I) or fatty acid salts thereof and ground dry pupa of silkworms.

The invention is further illustrated by the following non-limiting examples.

EXAMPLE 1

Attractiveness of various edible compositions

A filter paper, 15 cm in diameter, is placed close to the nest of *Monomorium pharaonis*. Six to seven of each 0.2 g of the bait compositions are placed on the filter paper along the circumference. The number of ants carrying the baits during five minutes after treatment are recorded using indications of −, ±, +, ++, +++, ++++. The quantity of baits remaining after 24 hours are weighed and also recorded. The results of these experiments which are summarized in Table I below demonstrate the effectiveness of the compositions of the invention for attracting these ants.

TABLE I

| Attractant/carrier evaluation | | |
|---|---|---|
| Bait attractant/carrier | Ants carrying during 5 min | Bait remaining after 24 hours |
| Ground dry pupa of silkworm | ++++ | 0 |
| Blood meal | − | most remained |
| Bone meal | − | most remained |
| Soybeans | − | most remained |
| Fishmeal | ++ | half remained |
| Corn grits | − | most remained |
| Meat extract | − | most remained |
| Flour | − | most remained |
| Ground krill | − | most remained |
| Dried daphnia | + | ⅔ remained |
| Dried shrimp | − | most remained |
| Cheese | + | half remained |
| 10% Honey + Fishmeal | + | ¼ remained |
| 10% Sugar + Fishmeal | + | ⅔ remained |
| 1% Eugenol + Fishmeal | ± | most remained |
| 0.1% Carbitol + Fishmeal | ± | most remained |
| 10% Carbitol + Fishmeal | − | most remained |
| 5% Malic acid + Fishmeal | ± | most remained |
| 5% Citric acid + Fishmeal | + | ⅔ remained |
| 5% Succinic acid + Fishmeal | ± | most remained |
| 5% Tartaric acid + Fishmeal | − | most remained |
| 5% Benzoic acid + Fishmeal | ± | most remained |
| 5% Sodium citrate + Fishmeal | − | most remained |
| 5% Sodium succinate + Fishmeal | − | most remained |
| 5% Sodium tartrate + Fishmeal | ± | most remained |
| 4.6% Sodium glutamate + 0.4% Sodium inosinate + Fishmeal | ++ | half remained |
| 4.6% Sodium glutamate + 0.4% Sodium inosinate + Corn grits | − | most remained |
| 2% Yellow dye + Fishmeal | ± | most remained |
| 5% Meat extract + Fishmeal | ++ | half remained |

TABLE I-continued

Attractant/carrier evaluation

| Bait attractant/carrier | Ants carrying during 5 min | Bait remaining after 24 hours |
|---|---|---|
| 1% Eugenol + Corn grits | — | most remained |
| 1% Carbitol + Corn grits | — | most remained |
| 70% Ground dry pupa of silkworm + 30% Fishmeal | ++++ | 0 |
| 70% Ground dry pupa of silkworm + 30% sugar | ++++ | 0 |

EXAMPLE 2

Preparation of granular insecticidal bait compositions

Ten kg of dry pupa of silkworm is ground using a rotary disc type grinder and screened using 10 and 60 mesh screens. A solution of 373.5 g composed of 25% tetrahydro-5,5-dimethyl-2(1H)-pyrimidinone-{3-[4-(trifluoromethyl)phenyl]-1-{2-[4-(trifluoromethyl)phenyl]ethenyl}-2-propenylidene}hydrazone, 25% oleic acid and 50% corn oil is sprayed onto the tumbling pupa, and the mixture blended until homogeneous.

EXAMPLE 3

Preparation of granular bath composition

The ingredients listed in Table II below totaling 100 g are placed in a mortar and blended well. Then the mixture is chopped using chopper in which straight blade is rotating to maximize 10 to 60 mesh particle size. The product is collected using screens to give the granular bait compositions listed in Table II.

TABLE II

Granular insecticidal bait compositions

| Composition No | Active ingredient | Attractants/carriers | % | Anti-oxidant | Anti-microbial agent |
|---|---|---|---|---|---|
| 1 | tetrahydro-5,5-dimethyl-2(1H)—pyrimidinone-{3-[4-(trifluoromethyl)phenyl-1-{2-[4-trifluoromethyl)phenyl]ethenyl}-2-propenylidene}hydrazone | Dry pupa of silkworm<br>Fishmeal<br>Powdered sugar<br>Flour<br>Rice bran oil | 55.0<br>20.0<br>16.9<br>3.0<br>4.0 | tert-butyl hydroquinone 0.1% | Na—salcylate 0.1% |
| 2 | tetrahydro-5,5-dimethyl-(2H)—pyrimidinone-{3-[4-(trifluoromethyl)phenyl-1-{2-[4-(trifluoromethyl)phenyl]ethenyl}-2-propenylidene}-hydrazone | Dry pupa of silkworm<br>Fishmeal<br>Powdered sugar<br>Flour<br>Rice bran oil | 18.0<br>50.0<br>2.7<br>2.1<br>2.0 | 0 | 0 |
| 3 | tetrahydro-5,5-dimethyl-2(1H)—pyrimidinone-{3-[4-(trifluoromethyl)phenyl-1-{2-[4-trifluoromethyl)phenyl]-ethenyl}-2-propenylidene}hydrazone | Dry pupa of silkworm<br>Fishmeal<br>Flour<br>Oleic acid | 70.0<br>25.1<br>20.0<br>3.0 | 0 | 0 |
| 4 | tetrahydro-5,5-dimethyl-2-(1H)—pyrimidinone-{3-[4-(trifluoromethyl)phenyl-1-{2-[4-trifluoromethyl)phenyl]-ethenyl}-2-propenylidene}hydrazone | Dry pupa of silkworm<br>Krill powder<br>Flour<br>Oleic acid | 70.0<br>25.1<br>2.0<br>2.0 | 0 | 0 |
| 5 | tetrahydro-5,5-dimethyl-2(1H)—pyrimidinone-{3-[4-(trifluoromethyl)phenyl-1-{2-[4-(trifluoromethyl)phenyl]-ethenyl}-2-propenylidene}hydrazone | Dry pupa of silkworm<br>Glucose<br>Flour<br>Oleic acid | 70.0<br>15.1<br>12.1<br>2.0 | 0 | 0 |
| 6 Control | tetrahydro-5,5-dimethyl-2(1H)—pyrimidinone-{3-[4-(trifluoromethyl)phenyl-1-{2-[4-(trfluoromethyl)phenyl]-ethenyl}-2-propenylidene}hydrazone | Corn grit | 99.1 | 0 | 0 |

EXAMPLE 4

Effectiveness of granular insecticidal bait compositions

A filter paper, 3 cm in diameter containing 0.5 g of the granular insecticidal bait compositions prepared in Examples 2 and 3 is placed close to the nests of various ant species. The baits are examined one day after placement and the amount of bait recorded. One week after placement the area surrounding each treatment is examined for the presence of ants in the vicinity of the treated area recorded.

The results of these experiments which are summarized in Table III below demonstrate the improved effectiveness of granular insecticidal bait compositions of the inventions compared to the control composition (Examples 3–6).

Results comparable to those obtained for composition 1 are also obtained using the antioxidants n-propyl gallate, 3-tert -butyl-4-hydroxy anisole and dibutyl hydroxy toluene or the antimicrobial agent sodium dehydroacetate.

or 0.1% by weight tert-butylhydroquinone or butylated hydroxytoluene.

6. A composition according to claim 3 comprising on a weight basis 30% to 50% of ground dry pupa of silkworms, 0.5% to 3.0% of the formula (I) insecticide, 10% to 20% fishmeal, 25% to 40% powdered sugar, 0.1% sodium salicylate, 0.2% tert butylhydroquinone, and 0.1% of the sodium salt of carboxymethylcellulose.

TABLE III

| | Evaluation of granular bait compositions | | | | |
|---|---|---|---|---|---|
| Composition | Ant species | Lasius nigar | Pheidole nodus | Tetramorium caespitum | Monomorium pharaonis |
| Example 2 | Bait remaining (one day) | 0 | 0 | 0 | 0 |
| | ants observed | disappeared | disappeared | disappeared | disappeared |
| Example 3-1 | Bait remaining (one day) | 0 | — | 0 | 0 |
| | ants observed | disappeared | | disappeared | disappeared |
| Example 3-2 | Bait remaining (one day) | 0 | — | 0 | 0 |
| | ants observed | disappeared | | disappeared | disappeared |
| Example 3-3 | Bait remaining (one day) | 0 | 0 | 0 | 0 |
| | ants observed | disappeared | disappeared | disappeared | disappeared |
| Example 3-4 | Bait remaining (one day) | 0 | 0 | 0 | 0 |
| | ants observed | disappeared | disappeared | disappeared | disappeared |
| Example 3-5 | Bait remaining (one day) | 0 | 0 | 0 | 0 |
| | ants observed | disappeared | disappeared | disappeared | disappeared |

What is claimed is:

1. A granular insecticidal bait composition comprising 0.5% to 5% tetrahydro-5,5-dimethyl-2-(1H)-pyrimidinone-{3-[4-(trifluoromethyl)phenyl]-1-{2-[4-(trifluoromethyl)-phenyl]ethenyl}-2-propenylidene}hydrazone having the formula (I)

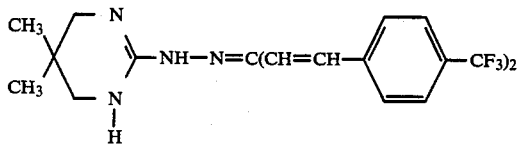

or fatty acid salt thereof and 95% to 99.5% ground dry pupa of silkworms.

2. A granular insecticidical bait composition comprising on a weight basis 15% to 70% ground dry pupa of silkworms, 0.5% to 5% tetrahydro-5,5-dimethyl-2-(1H)-pyrimidinone-(3-[4-(trifluoromethyl)phenyl]-1-{2-[4-(trifluoromethyl)-phenyl]ethenyl}-2-propenylidene} hydrazone having the formula (I)

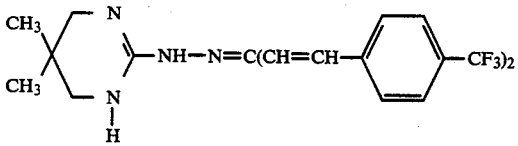

or fatty acid salt thereof, 0.0% to 5.0% of oleic acid, 29.5% to 75% of a solid or liquid carrier, and 0% to 0.5% of an antimicrobial agent, anioxidizing agent or mixtures thereof.

3. A composition according to claim 2 wherein the carrier is an edible carrier of fishmeal, powdered sugar, flour, krill, corn grits, corn syrup, rice oil, corn oil, soybean oil, glucose or mixtures thereof.

4. A composition according to claim 3 wherein the carrier is fishmeal.

5. A composition according to claim 3 containing 0.1% by weight sodium salicylate or sodium benzoate;

7. A method for controlling ants comprising applying in the vicinity of their habitat or infested area an insecticidally effective amount of a granular insecticidal bait composition comprising 0.5% to 5% tetrahydro-5,5-dimethyl-2-(1H)-pyrimidinone-{-3-[4-(trifluoromethyl)-phenyl]-1-{2-[4-(trifluoromethyl)phenyl]ethenyl}-2-propenylidene}hydrazone having the formula (I)

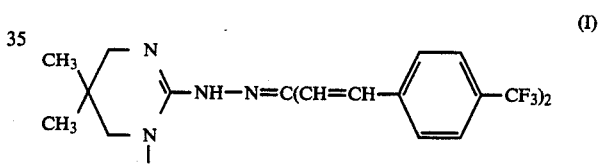

or fatty acid salt thereof and 95% to 99.5% ground dry pupa of silkworms.

8. A method for controlling ants comprising applying in the vicinity of their habitat or infested area an insecticidally effective amount of a granula insecticidal bait composition comprising on a weight basis 15% to 70% ground dry pupa of silkworms, 0.5% to 5% tetrahydro-5,5-dimethyl-2-(1H)-pyrimidinone-{-3-[4-(trifluoromethyl)phenyl]-1-{2-[4-(trifluoromethyl)-phenyl]ethenyl}-2-propenylidene}hydrazone having the formula (I)

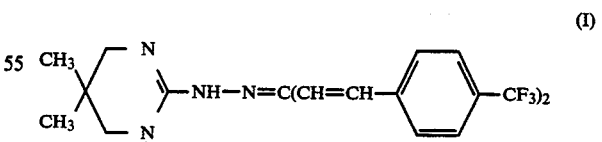

or fatty acid salt thereof, 0.0% to 5.0% of oleic acid, 29.5% to 75% of a solid or liquid carrier, and 0% to 0.5% of an antimicrobial agent, antioxidizing agent or mixtures thereof.

9. A method according to claim 8 wherein the edible carrier is fishmeal, powdered sugar, flour, krill, corn grits, corn syrup, rice oil, corn oil, soybean oil, glucose or mixtures thereof.

10. A method according to claim 9 wherein the carrier is fishmeal.

11. A method according to claim 9 wherein the composition contains 0.1% by weight sodium salicylate or sodium benzoate; or 0.1% by weight tert-butylhydroquinone or butylated hydroxytoluene.

12. A method according to claim 8 comprising on a weight basis 30% to 50% of ground dry pupa of silkworms, 0.5% to 3.0% of the formula (I) insecticide, 10% to 20% fishmeal, 25% to 40% powdered sugar, 0.1% sodium salicylate, 0.2% tert butylhydroquinone, and 0.1% of the sodium salt of carboxymethylcellulose.

* * * * *